(12) United States Patent
Oost et al.

(10) Patent No.: US 6,784,303 B2
(45) Date of Patent: Aug. 31, 2004

(54) METHOD FOR CONTINUOUSLY ACYLATING CHROMANOL ESTER DERIVATIVES

(75) Inventors: Carsten Oost, Bad Dürkheim (DE); Gerd Kaibel, Lampertheim (DE); Harald Laas, Maxdorf (DE); Peter Schmitt, Lambsheim (DE); Jens von Erden, Altrip (DE)

(73) Assignee: BASF Aktiengesellschaft, Ludwigshafen (DE)

( * ) Notice: Subject to any disclaimer, the term of this patent is extended or adjusted under 35 U.S.C. 154(b) by 0 days.

(21) Appl. No.: 10/416,468

(22) PCT Filed: Nov. 21, 2001

(86) PCT No.: PCT/EP01/13472

§ 371 (c)(1),
(2), (4) Date: May 12, 2003

(87) PCT Pub. No.: WO02/42286

PCT Pub. Date: May 30, 2002

(65) Prior Publication Data

US 2004/0014996 A1 Jan. 22, 2004

(30) Foreign Application Priority Data

Nov. 22, 2000 (DE) ......................................... 100 58 132

(51) Int. Cl.⁷ ........................................... C07D 311/76
(52) U.S. Cl. ....................... 549/408; 549/410; 549/412
(58) Field of Search ................................. 549/408, 410, 549/412

(56) References Cited

U.S. PATENT DOCUMENTS

| | | |
|---|---|---|
| 3,444,213 A | 5/1969 | Nelan |
| 3,708,505 A | 1/1973 | Greenbaum et al. |
| 5,468,883 A | 11/1995 | Grafen et al. |
| 5,886,196 A | 3/1999 | Furbringer |
| 6,005,122 A | 12/1999 | Baldenius et al. |
| 6,365,758 B1 * | 4/2002 | von dem Bussche-Hunnefeld et al. ............................. 549/410 |

FOREIGN PATENT DOCUMENTS

| | | |
|---|---|---|
| CZ | 205 951 | 5/1984 |
| DE | 2 208 795 | 8/1972 |
| DE | 2 208795 | 8/1972 |
| DE | 42 08 477 | 9/1993 |
| DE | 196 03142 | 7/1997 |
| EP | 784 042 | 7/1997 |
| EP | 850 937 | 7/1998 |
| WO | 93/19057 | 9/1993 |
| WO | 97/28151 | 8/1997 |

OTHER PUBLICATIONS

Chem.Abst. XP–002197863.

Chem.Abst. XP–002197864.

Abstract JP 49 055 633.

Ullmann's Enc.Ind.Chem.vol. 27 (1996) 478–488,Chap. 4.

* cited by examiner

*Primary Examiner*—Rita Desai
*Assistant Examiner*—Robert Shiao
(74) *Attorney, Agent, or Firm*—Keil & Weinkauf

(57) ABSTRACT

A process is described for continuously preparing chromanol ester derivatives, in particular for continuously preparing carboxylic esters of tocopherols and tocotrienols by continuous acylation with carboxylic acids or carboxylic anhydrides.

13 Claims, 2 Drawing Sheets

METHOD FOR CONTINUOUSLY ACYLATING CHROMANOL ESTER DERIVATIVES

The present invention relates to a process for continuously preparing chromanol ester derivatives, in particular for continuously preparing carboxylic esters of tocopherols and tocotrienols by continuous acylation with carboxylic acids or carboxylic anhydrides.

Compounds having vitamin E activity, such as the naturally occurring chromanol derivatives of the tocopherol and tocotrienol group, are important fat-soluble antioxidants. A vitamin E deficiency in humans and animals leads to pathophysiological conditions. Vitamin E compounds therefore have a high economic value as additives in the food and feed sectors, in pharmaceutical formulations and in cosmetics applications. The compounds having vitamin E activity, in particular α-tocopherol, are used for this principally in the form of their acetate esters. An economic process for preparing chromanol ester derivatives is therefore of high importance.

It is known to react tocopherol derivatives batchwise with acetic anhydride to give the corresponding acetate esters.

EP 850 937 describes in the examples a batchwise process for preparing α-tocopherol acetate by heating under reflux α-tocopherol with acetic anhydride in a stirred flask having an attached reflux condenser. The reaction discharge is then worked up by distillation.

DE 19 603 142 describes a process for preparing dl-α-tocopherol acetate by acid-catalyzed reaction of 2,3,5-trimethylhydroquinone (TMH) with phytol or isophytol (IP) in a solvent at elevated temperature and subsequent acetylation of the resultant tocopherol. The tocopherol is acetylated by acid-catalyzed reaction with excess acetic anhydride. The reaction discharge is worked up by fractional distillation under reduced pressure. For the continuous reaction of 2,3,5-trimethylhydroquinone with phytol, a reaction column is proposed into which a mixture of cyclic carbonate, the catalyst, TMH and IP are fed in laterally. The hydrocarbon and the water formed are removed at the top of the column and hot cyclic carbonate and vitamin E are taken off from the bottom. No description is given of the process design of the subsequent acylation. An example mentions that the tocopherol isolated after phase separation was esterified with acetic anhydride.

A process for preparing dl-α-tocopherol or dl-α-tocopherol acetate by acid-catalyzed reaction of 2,3,5-trimethylhydroquinone (TMH) with phytol or isophytol (IP) in the presence of a mixture of orthoboric acid and certain aliphatic di- or tricarboxylic acids with or without subsequent esterification with acetic anhydride is described in DE 42 08 477. According to DE 42 08 477, the tocopherol prepared is converted in a similar manner to DE 19 603 142 into tocopherol acetate batchwise with excess acetic anhydride under acid catalysis and purified by fractional distillation under a greatly reduced pressure. The initial molar ratio of acetic anhydride/tocopherol was greater than 1.3 mol/mol and the acid concentration was approximately 0.055 mol % based on tocopherol.

EP 0 784 042 claimed hydrogen bis(oxalato)borate as protic acid catalyst for the Friedel-Crafts condensation of trimethylhydroquinone with isophytol and the acylation of phenols, for example tocopherol. In an example the acylation of tocopherol is described. For this, tocopherol was charged into a flask together with acetic anhydride and hydrogen bis(oxalato)borate and the reaction mixture was heated to reflux for one hour under an argon atmosphere. The initial molar ratio of acetic anhydride/tocopherol was greater than 1.1 mol/mol and the borate concentration was approximately 0.5 mol %, based on tocopherol. After concentration on a rotary evaporator, tocopherol acetate was obtained in a purity of 87% at a yield of 92%. This batch process has the disadvantage that both yield and purity are still not satisfactorily high. In addition, carrying out the reaction in an argon atmosphere is associated with high costs for industrial production.

JP 49 055 633 describes the batchwise preparation of tocopherol acetate by acylation of tocopherol with acetic anhydride in the presence of inorganic solid acids which are insoluble in the reaction mixture. In the process, tocopherol and acetic anhydride in the solvent toluene are heated in the presence of the catalyst for about 4 hours under reflux, a product purity of about 91% being achieved. As an example of the catalyst, $SiO_2/Al_2O_3$ is mentioned. Disadvantages of the process are the low space-time yields and the low product purities.

The acylation of tocopherol with acetic anhydride in the presence of a mixture of hydrochloric acid and zinc or zinc chloride is described in JP 56 073 081. According to this process, tocopherol is heated with acetic anhydride and the catalyst mixture at from 10 to 30° C. for from 0.5 to 2 hours. The catalyst is then removed and the reaction mixture is washed with water. Hydrochloric acid is used at a concentration of from 0.02 to 0.06 mol % based on tocopherol, the zinc is used at a concentration of from 0.01 to 0.2 mol % based on tocopherol and the zinc chloride is used at a concentration of from 0.001 to 0.1 mol % based on tocopherol. Acetic anhydride is used at a from 1.2 to 1.5 times molar excess. The process gives tocopherol acetate at a yield of 92.5% based on tocopherol. The complex workup, the batchwise reaction procedure and the solids handling cause a low space-time yield in this process, despite the short reaction time.

DE 2 208 795 describes the reaction of trimethylhydroquinone with isophytol in the presence of a mixture of a Lewis acid and a protic acid in an inert solvent. The catalyst system which can be used is, for example, a mixture of zinc chloride with $NaHSO_4$, $H_2SO_4$ or p-toluenesulfonic acid. Optionally, the reaction discharge can be reacted with acetic anhydride without further workup. For this acetic anhydride is added to the reaction mixture and heated under reflux for about 6 hours. A disadvantage of this process is the low space-time yield for the acylation.

A continuous process for reacting trimethylhydroquinone with isophytol, phytol or phytadienes in the presence of acid condensation catalysts in a packed column is described in U.S. Pat. No. 3,444,213. In this process the reactants, optionally premixed or dissolved in an inert solvent, are applied to the top of a heated column and the resultant reaction water is evaporated via the top of the column. The column, however, is only a heated tubular reactor without evaporator, and not a reactive distillation column. The product arising at the bottom of the column is reacted in the course of one hour batchwise with acetic anhydride in the solvent pyridine. A disadvantage of this process is the low space-time yield of the acylation and the use of a solvent.

A further continuous process for reacting trimethylhydroquinone with isophytol is described in CS 205 951. In this patent also, the acylation is performed batchwise using acetic anhydride.

All known processes of the prior art for acetylating tocopherol derivatives have the disadvantage of high residence times and thus low space-time yields and high capital costs. In all cases the tocopherol derivative, in the absence or presence of a catalyst, is reacted batchwise with acetic anhydride and the reaction mixture is worked up by distillation. In this case, firstly the acetic acid and the acetic anhydride are removed at low vacuum and the acetate of the tocopherol derivative is then purified by distillation under a high vacuum.

Furthermore, the yields of these processes, at about from 92 to 95%, are insufficiently satisfactory. The acetic anhydride is always used in a relatively high excess of at least 1.2 mol per mole of tocopherol derivative, in order to achieve a sufficient conversion rate at an acceptable reaction time. As implied by EP 0 784 042, reduction in the excess of acetic anhydride is only possible if the acid concentration is considerably increased. However, this leads to an increased formation of byproducts and thus to decreased yields and product purity.

It is an object of the present invention, therefore, to provide a further process for preparing chromanol ester derivatives having advantageous properties, which process no longer exhibits the disadvantages of the prior art and which gives chromanol ester derivatives in high yields and high space-time yields.

We have found that this object is achieved by a process for continuously preparing chromanol ester derivatives of the formula I,

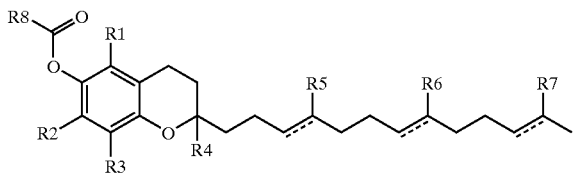

I where

R1, R2, R3, R4, R5, R6, R7 and R8 independently of one another are hydrogen or an unsubstituted or substituted, branched or unbranched $C_1$–$C_{10}$–alkyl radical and the dashed bonds are a possible additional C—C bond, by reacting continuously fed chromanol derivatives of the formula II

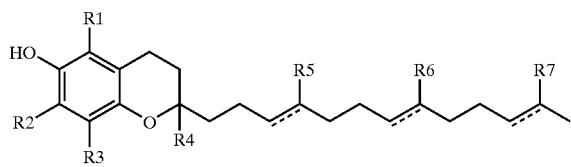

II with continuously fed acylating agent selected from the group consisting of carboxylic acids of the formula IIIa

    IIIa and carboxylic anhydrides of the formula IIIb,

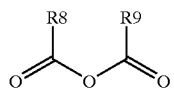    IIIb where

R9 is hydrogen or an unsubstituted or substituted, branched or unbranched $C_1$–$C_{10}$-alkyl radical, in a reactor and continuously removing the reaction products from the reactor.

An unsubstituted or substituted, branched or unbranched $C_1$–$C_{10}$-alkyl radical is, for the radicals R1, R2, R3, R4, R5, R6, R7, R8 and R9 independently of one another, for example, unsubstituted or substituted methyl, ethyl, propyl, 1-methylethyl, butyl, 1-methylpropyl, 2-methylpropyl, 1,1-dimethylethyl, pentyl, 1-methylbutyl, 2-methylbutyl, 1,2-dimethylpropyl, 1,1-dimethylpropyl, 2,2-dimethylpropyl, 1-ethylpropyl, hexyl, 1-methylpentyl, 1,2-dimethylbutyl, 1,3-dimethylbutyl, 2,3-dimethylbutyl, 1,1-dimethylbutyl, 2,2-dimethylbutyl, 3,3-dimethylbutyl, 1,1,2-trimethylpropyl, 1,2,2-trimethylpropyl, 1-ethylbutyl, 2-ethylbutyl, heptyl, octyl, nonyl or decyl, preferably unsubstituted or substituted $C_1$–$C_4$-alkyl, for example methyl, ethyl, isopropyl, n-propyl, n-butyl, sec-butyl or tert-butyl.

The type of substituents is not critical. The $C_1$–$C_{10}$-alkyl radicals, depending on free bonds available, can contain up to 6 substituents, preferably selected from the group consisting of —$NO_2$, —$NH_2$, —OH, —CN, —COOH, or halogen, in particular F or Cl.

In a preferred embodiment the branched or unbranched $C_1$–$C_{10}$-alkyl radicals of the radicals R1, R2, R3, R4, R5, R6, R7, R8 and R9 are not substituted.

Particularly preferred radicals for R4, R5, R6 and R7 are independently of one another hydrogen or methyl, in particular methyl.

Particularly preferred radicals for R1, R2 and R3 are independently of one another hydrogen or methyl.

Particularly preferred radicals for R8 are methyl or ethyl, in particular methyl.

Particularly preferred radicals for R9 are ethyl or methyl.

In a preferred embodiment of the inventive process, the chromanol derivatives of the formula II are tocopherol derivatives and tocotrienol derivatives having vitamin E activity, in particular the naturally occurring tocopherols and tocotrienols.

For the preferred naturally occurring tocopherols and tocotrienols, in formula II the radicals R4 to R7 are methyl. The group of tocopherols (IIa–d) has a saturated side chain, and the group of the tocotrienols (IIe–h) have an unsaturated side chain:

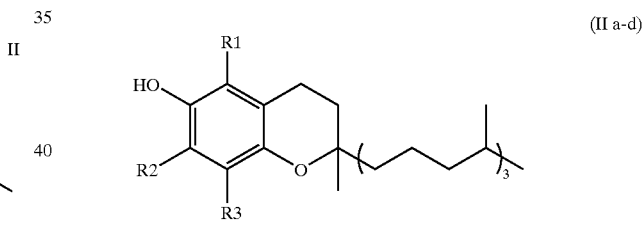

(II a-d)

IIa, α-Tocopherol: R1 = R2 = R3 = $CH_3$
IIb, β-Tocopherol: R1 = R3 = $CH_3$, R2 = H
IIc, γ-Tocopherol: R1 =H, R2 = R3 = $CH_3$
IId, δ-Tocopherol: R1 = R2 = H, R3 = $CH_3$

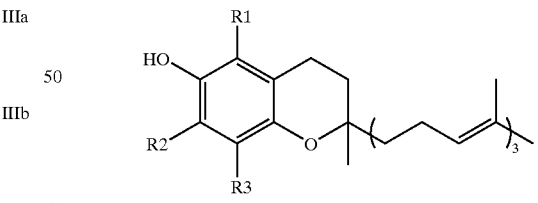

(II e-h)

IIe, α-Tocotrienol: R1 = R2 = R3 = $CH_3$
IIf, β-Tocotrienol: R1 = R3 = $CH_3$, R2 = H
IIg, γ-Tocotrienol: R1 =H, R2 = R3 = $CH_3$
IIh, δ-Tocotrienol: R1 = R2 = H, R3 = $CH_3$ Particularly preferably, in the inventive process α-tocopherol of the formula IIa is used as chromanol derivative of the formula II.

The chromanol derivatives of the formula II used in the inventive process, in particular the preferred tocopherols and tocotrienols of the formulae IIa to IIh can be used as individual compounds which can be present in any desired purity. Generally, the purity of individual tocopherols and tocotrienols is from 90% to 97%, but purer compounds and less pure crude products can also be used. The compounds can also be used as a mixture of different chromanol derivatives of the formula II and the inventive process correspondingly leads to a mixture of chromanol ester derivatives of the formula I. This can be the case, for example, when tocopherols or tocotrienols are used from natural sources without further separation of the individual tocopherols and tocotrienols. The chromanol derivatives of the formula II can be enantiomerically pure, a racemic mixture, or a diastereomer mixture.

The chromanol derivatives of the formula II can be chemically prepared or isolated from natural sources, for example the evaporator condensates produced in vegetable oil deodorization and purified, as described in Ullmann's Encyclopedia of Industrial Chemistry, Vol. A 27 (1996), VCH Verlagsgesellschaft, Chapter 4., 478–488, Vitamin E.

The carboxylic acids of the formula IIIa or carboxylic anhydrides of the formula IIIb used as acylating agents in the inventive process can be used as individual substances or as mixtures.

In a preferred embodiment, the acylating agents used are the carboxylic anhydrides of the formula IIIb.

The carboxylic anhydrides of the formula IIIb can be used as pure carboxylic anhydrides or as mixed carboxylic anhydrides. In a preferred embodiment, pure carboxylic anhydrides are used, so that R8=R9. Particular preference is given to the acetylation using acetic anhydride as carboxylic anhydride of the formula IIIb where R8=R9=methyl.

In the inventive process the reactants, the chromanol derivatives of the formula II and the acylating agents, selected from the group consisting of carboxylic acids of the formula IIIa and carboxylic anhydrides of the formula IIIb, are fed continuously to a reactor, reacted in the reactor and then the reaction products are continuously removed from the reactor.

In the case of reactions having a high initial rate, it can be advantageous to connect upstream of the reactor a further preliminary reactor in which a partial conversion already takes place. It can also be advantageous to mix the reactants before feeding into the reactor, so that here also a partial conversion takes place.

The term "reacted in a reactor" therefore means that in this reactor conversion of the reactants still takes place. This conversion in the reactor can, for example when a preliminary reactor is connected upstream, be at least 1%, preferably at least 20%, particularly preferably at least 50%, very particularly preferably at least 80%, of the conversion rate which is achievable overall. In a preferred embodiment, the total achievable conversion occurs in the reactor.

When the reactants are fed and reacted, in addition solvents can be used. Particularly advantageously, however, the process may be carried out without addition of solvents.

The inventive process may be particularly advantageously carried out by continuously removing at least one reaction product from the reaction mixture during the reaction in the reactor, that is to say simultaneously with the reaction. Accordingly, the water formed from the acylating agent (when carboxylic acids of the formula IIIa are used as acylating agent) or the resultant carboxylic aci R9-COOH (when carboxylic anhydrides of the formula IIIb are used as acylating agent) or the resultant chromanol ester derivatives of the formula I or both are removed from the reaction mixture during the reaction.

In a preferred embodiment, only water or the carboxylic acid R9-COOH is removed from the reaction mixture. This removal is also preferably performed continuously.

There are many reactor designs which come into consideration for the preferred inventive process. Preferred reactors should have the property of enabling continuous reaction with simultaneous removal of at least one reaction product. For example, reactors which can be used are stills having an attached column, divided wall columns, extraction columns, membrane reactors or reaction columns.

In a particularly preferred embodiment of the inventive process, the reaction is performed in a reaction column as reactor.

As described above, it can be advantageous to connect upstream of this reaction column a reactor (preliminary reactor) in which a portion of the conversion already takes place. In a particularly preferred embodiment, the reaction is performed in a reactor, in particular in a reaction column.

A reaction column, which can be designed in very different ways, has the property as a reactor of enabling simultaneously a reaction of reactants and the thermal removal of at least one reaction product.

Preferably the reaction column consists of a bottom and a superstructure which enables rectification, for example a fractionation column.

In this preferred embodiment, using a reaction column it is further advantageous to set the reaction parameters in such a manner that A the chromanol derivatives of the formula II react with the acylating agent on the internals and possibly in the bottom phase of the reaction column, B the $H_2O$ formed in the reaction with the acylating agent (use of carboxylic acids of the formula IIIa as acylating agent) or the carboxylic acid R9-COOH formed (use of carboxylic anhydrides of the formula IIIb as acylating agent) is continuously removed with the overhead stream of the reaction column and C the chromanol ester derivatives of the formula I formed in the reaction are continuously removed with the bottom stream of the reaction column.

Depending on the type of design of the reaction column and the reactants used, this is achieved by varying reaction parameter settings. Suitable reaction parameters are, for example, temperature, pressure, reflux ratio in the column, design of the column, heat transfer and residence time, in particular in the bottom phase, energy input or the molar ratio of the reactants, which can be optimized by those skilled in the art by routine experiments so that the features A, B and C are achieved.

Typically, in the inventive process, the pressure at the column top is set so that the temperature in the bottom is from 100 to 300° C. preferably from 130 to 180° C.

The residence time in the reaction column is typically from 15 minutes to 6 hours, preferably from 30 minutes to 3 hours.

The initial ratio of the reactants is not critical, the molar ratio of acylating agent, that is to say the carboxylic acids of the formula IIIa or the carboxylic anhydrides of the formula IIIb to the chromanol derivative of the formula II is usually from 1.0 to 5.0, preferably from 1.0 to 1.3.

The inventive process may be carried out particularly advantageously if the reaction is carried out in the presence of a catalyst.

A catalyst is a substance which is able to accelerate the acylation of chromanol derivatives of the formula II.

Preferred catalysts are acid or basic acylation catalysts, for example, sulfuric acid, phosphoric acid, hydrochloric acid, acetic acid, acetates, zinc chloride, triethylamine, pyridine, tertiary bases, hydrogen bis(oxalato)borate, acid or basic ion exchangers, zeolites, $SiO_2/Al_2O_3$ or inorganic solid acids.

Particularly preferred catalysts are homogeneous basic or acid catalysts, in particular sulfuric acid or phosphoric acid, and heterogeneous catalysts, in particular acid ion exchangers or acid zeolites, which are introduced in a targeted manner into the reaction zone.

The homogeneous catalysts have the advantage that they can be pumped in the liquid state into the fractionation column. The heterogeneous catalysts have the advantage that they do not lead to contamination of the product or to impairment of the color index of the product during workup.

The homogeneous catalysts are preferably used in dilute form. Thus, for example, sulfuric acid and phosphoric acid are typically used at a concentration from 0.01 to 50%, preferably at a concentration from 0.1 to 1.0%. The amount of the homogeneous catalysts is preferably dimensioned such that their concentration is from 0.001 to 1.0 mol %, based on the chromanol derivative of the formula II, preferably from 0.01 to 0.1 mol %, based on the chromanol derivative of the formula II.

The heterogenous catalysts are preferably integrated into the fractionation column internals.

In a particularly preferred embodiment of the inventive process, the reaction column internals used are column trays below the highest feed point for the reactants, and are structured packings above the highest feed point for the reactants. Particularly advantageous column trays make high residence time of the liquid possible, with the residence time on the reaction column internals preferably being at least 30 min.

Preferred column trays are, for example, valve trays, preferably bubble-cap trays, or related types, for example tunnel trays or Thormann trays.

Preferred structured packings are, for example, structured packings of the following types: Melapack$^{(R)}$ (Sulzer), BX$^{(R)}$ (Sulzer), B1$^{(R)}$ (Montz) or A3$^{(R)}$ (Montz) or packings of comparable designs.

In a further particularly preferred embodiment of the inventive process, the higher-boiling reactant, if appropriate together with the homogeneous catalyst, is fed into the reaction column above the lower-boiling reactant.

Particularly advantageously, the process may be carried out by the heat being fed into the reaction column, in addition to an evaporator, via heat exchangers mounted externally to the reaction column, or via heat exchangers situated directly on the column trays.

In addition, the introduction of a stripping gas, preferably nitrogen or carbon dioxide, into the reaction column is advantageous.

This facilitates the removal of water or the resultant carboxylic acid R9-COOH.

In addition, the inventive process may be carried out advantageously by removing excess acylating agent, that is to say the carboxylic acid of the formula IIIa or the carboxylic anhydride of the formula IIIb, from the effluent bottom stream in a downstream evaporator, and recirculating it to the column with or without ejection of a substream. As a result, high yields are achieved based on the acylating agent (carboxylic acid of the formula IIIa or carboxylic anhydride of the formula IIIb).

DETAILED DESCRIPTION OF THE DRAWINGS

Figure 1:
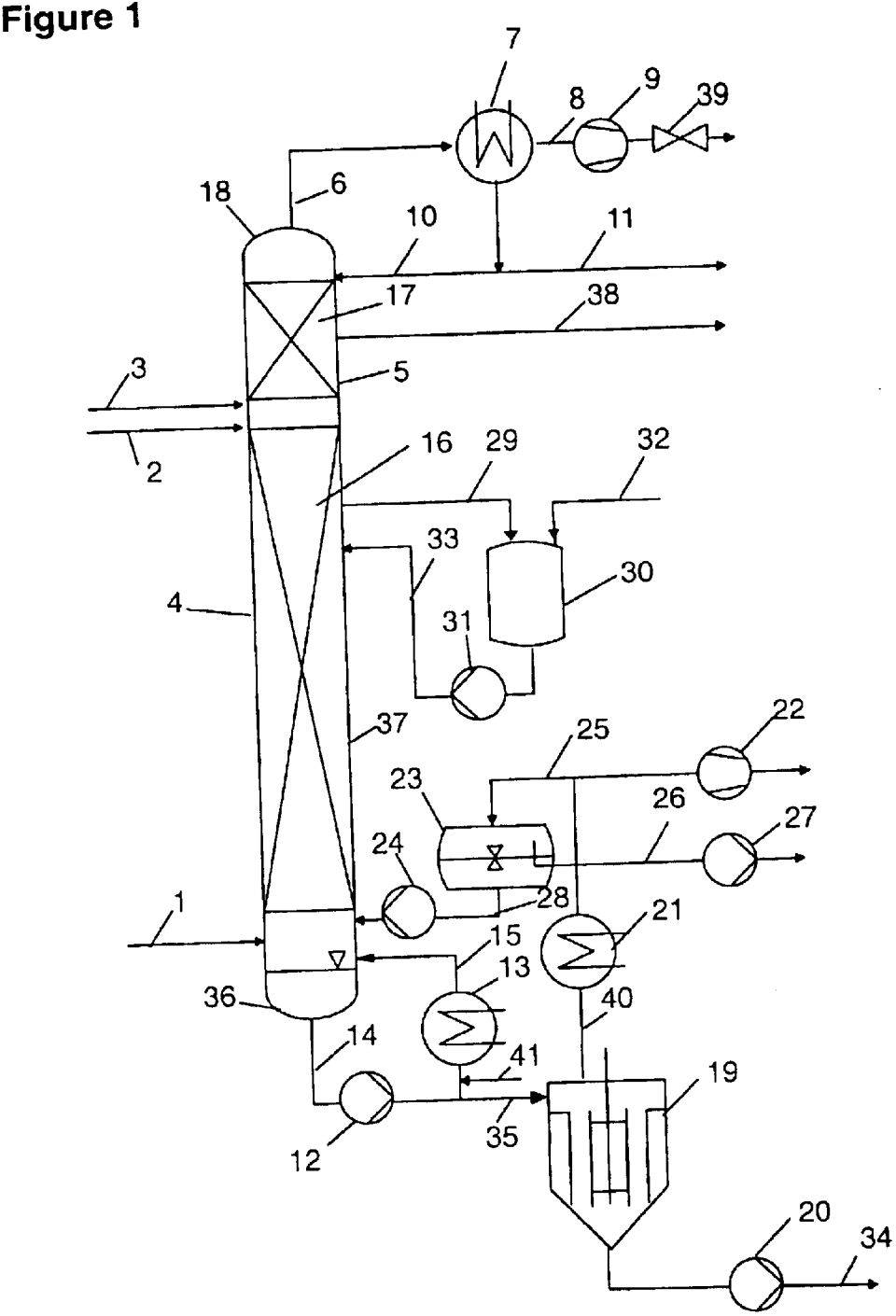
FIGS. 1 and 2 illustrate two particularly advantageous embodiments of the process.

A particularly advantageous embodiment of the inventive process will be described below by way of example with reference to FIG. 1:

The inventive process is preferably carried out in such a manner that the chromanol derivative of the formula II, the acylating agent (carboxylic acids of the formula IIIa or carboxylic anhydrides of the formula IIIb) with or without the catalyst is applied via the feeds (3), (1) and (2) to the internals of a fractionating column (4) functioning as a reaction column. It is advantageous here, but not obligatory, if the higher-boiling reactant is fed continuously into the fractionating column (4) separately or together with the catalyst above the lower-boiling reactant. On the fractionating column internals, the chromanol derivative of the formula II then reacts with the acylating agent, with a superimposed distillation. As a result the water forming from the carboxylic acid of the formula IIIa or the carboxylic acid R9-COOH forming from the carboxylic anhydride of the formula IIIb is constantly removed from the reaction equilibrium.

The chromanol ester derivatives of the formula I pass through the superimposed distillation into the bottom (36) of the fractionating column and are taken off via the stream (14).

When acetic anhydride or priopionic anhydride is used as carboxylic anhydride of the formula IIIb, it is very advantageous if this carboxylic anhydride is introduced into the column (4) in vaporous form, since cleavage in the bottom (36) of the column at high temperatures and formation of byproducts is further reduced to avoided.

In addition it has proved to be highly advantageous if the heat is fed into the reaction system consisting of the column bottom (36) and fractionating column (4) and possibly also vessel (30) not just via the evaporator (13) but additionally via external heat exchangers (37) or via heat exchangers situated directly on the column internals (16).

The reaction column (4) consists of two segments. The upper segment (17) is preferably packed with structured packings, and the lower segment (16) is preferably packed with column trays. It is advantageous to dimension the upper segment (17), depending on the separation effort, in such a manner that the acylating agent is completely retained and is recirculated to the lower segment (16) for reaction.

The water or the carboxylic acid R9-COOH formed leaves the column together with any low-boilers present in the reactants as contaminant or formed during the reaction as byproduct via the overhead stream (6) and passes into the condenser (7) where the condensable constituents of this vapor stream are condensed out. A part of the condensate is reapplied to the column as reflux (10) and the other part (11) is taken off.

The reflux ratio is not critical. Preferably, a reflux ratio from 1 to 20, particularly preferably from 2 to 4, should be set. However, it is also possible to take off the condensate completely (reflux ratio=0) if the higher-boiling reactant is applied at the upper end of the column.

The distillate (11) generally consists of water or the carboxylic acid R9-COOH in a purity greater than 99%. In the presence of low-boiling contaminants, it can be advantageous to take off the carboxylic acid R9-COOH at high purity via an additional side stream takeoff (38). For this, the upper column segment (17) must be dimensioned appropriately.

The pressure at the column top (6) is preferably set in such a manner that the temperature in the bottom (36) is from 100 to 300° C. in particular from 130 to 180° C. Depending on the system of substances, this can be achieved using a vacuum pump (9) and/or a pressure regulating device (39).

The reaction product collects in the bottom (36) of the column (4) and is taken off by means of a pump (12) via the bottom stream (14) together with the unreacted reactants, essentially together with excess carboxylic acid of the formula IIIa or excess carboxylic anhydride of the formula IIIb. A part of the bottom stream (14) is evaporated by an evaporator (13) and fed into the column via the vapor line (15). By this means the vapors required for the distillation are produced. The crude product is fed via the product line (35) to a downstream evaporator (19), which frees the crude product from low-boilers, in particular from unreacted carboxylic acid of the formula IIIa, or unreacted carboxylic anhydride of the formula IIIb.

It is possible, for removal of the resultant water or the carboxylic acid R9-COOH formed, to feed additionally an inert gas (41) into the bottom of the column.

The evaporator (19) is generally operated, using a vacuum unit (22) at a lower pressure than the column (4), the pressure being set in such a manner that the vapor stream (40) comprises only small amounts of product of value, and the product stream (34) comprises only small amounts of low-boilers. The vapor stream (40) of the evaporator (19) is condensed out in a condenser (21) and fed via the line (25) of the vessel (23).

In the case of mixtures of substances in which the carboxylic acid of the formula IIIa or water or the carboxylic anhydride of the formula IIIb or the carboxylic acid R9-COOH forms a miscibility gap with the minor components, the vessel (23) is designed as a phase-separation vessel.

In this case it is advantageous to eject the minor components using the pump (27) via the byproduct line (26) and in this manner to increase the selectivity and to prevent the accumulation of byproducts. The phase comprising unreacted reactants is recirculated to the column using a pump (24) via the line (28). If the condensed vapors (25) form a single phase, it can be advantageous to prevent an accumulation of byproducts by ejecting a part stream via the line (26).

Via the bottom stream (34) of the evaporator (19), the product of value freed from low-boilers is withdrawn and, if appropriate, fed to further purification stages such as short-path evaporators and/or molecular distillation.

The amounts added are preferably selected in such a manner that the stoichiometric ratio of acylating agent to the chromanol derivative of the formula II is from 1.0 to 5.0, preferably from 1.0 to 1.3, and a catalyst content is set from 0.001 to 1.0 mol %, preferably from 0.01 to 0.1 mol %, based on the chromanol derivative to be reacted.

The residence time of the reaction mixture in the reactor system consisting of bottom phase (36) and fractionating column (4) with or without vessel (30) is typically from 15 minutes to 6 hours, preferably from 20 minutes to 2 hours. This residence time may advantageously be achieved by trays (16, 17) having a high liquid residence time, for example valve trays, preferably bubble-cap trays or related types, for example tunnel trays or Thormann trays. However, it is also possible to use metal mesh packings or sheet metal packings having an ordered structure or else to use dumped packing beds as column internals.

In segment (17) above the feed site (3) preferably column internals having a high theoretical number of plates such as metal mesh packings or sheet metal packings having an ordered structure are used.

Furthermore, it is also advantageous, to increase the residence time, to pass a part stream through one or more side stream takeoffs (29) from the fractionating column (4) through the vessel or vessels (30) and to recirculate the part streams (33) leaving these vessels back to the column (4) using a pump (31) for each. If appropriate, additional catalysts and/or reactants can be added to the vessels (30) using a feed line (32).

Heating the vessels (30) is preferred.

To carry out the reaction, advantageously, fractionating columns are used which have as internals typically from 10 to 100 of the trays described in more detail above (16, 17), preferably from 20 to 40 trays. In this case the procedure is advantageously carried out in such a manner that the higher-boiling reactants are introduced into the upper part of the column and the lower-boiling reactants into the lower part of the column.

It has proved to be particularly advantageous if from 0 to 50 trays, preferably from 5 to 20 trays, are provided in the column above the feed stream (3) for the higher-boiling reactants and from 0 to 50, preferably from 5 to 30, trays are provided in the lower part of the column (16) below the feed stream (3).

The residence time on the column internals should be particularly preferably approximately 30 minutes. The same applies, correspondingly, for the theoretical plates in the case of other column internals.

Figure 2:
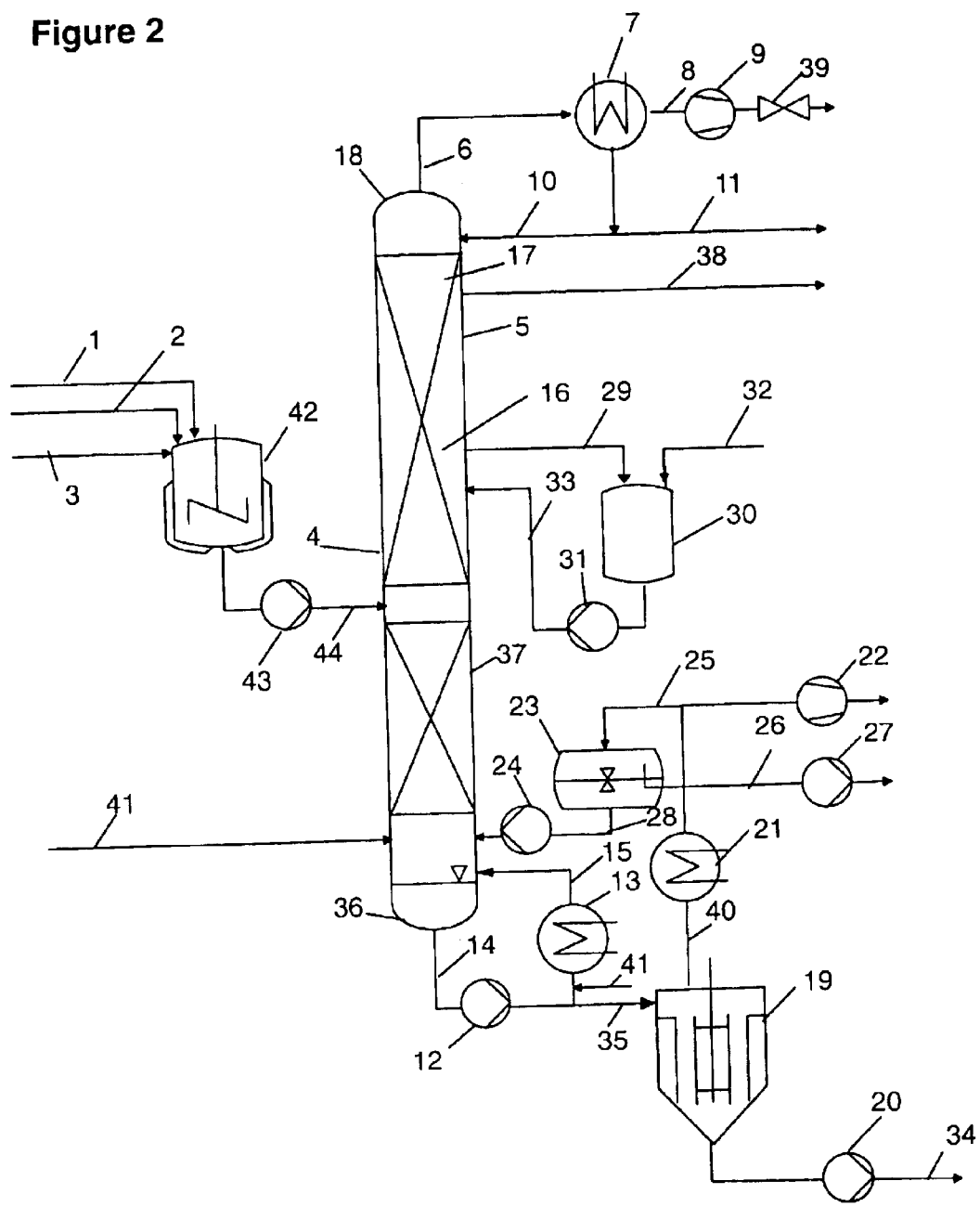

A further particularly preferred embodiment of the inventive process is shown in FIG. 2:

In particular in the case of reactions having a high initial rate, it can be advantageous to connect a reactor (42) upstream of the reaction column and in this manner to reduce the capital costs for the reaction column. For this the chromanol derivative of the formula II (3), the acylating agent (1) and, if appropriate, the catalyst (2) with or without preheating are pumped into the preliminary reactor (42). In this reactor, the reaction firstly proceeds with high initial rate.

In the preliminary reactor, preferably, only a partial conversion is sought and the discharge from the preliminary reactor is transported using the pump (43) via the line (44) into the downstream reaction column (4).

The reaction column (4), in this embodiment of the inventive process, is essentially designed as described in FIG. 1, in which case the feed point of the reactor discharge (44) into the column (4) must be adapated to the respective system of substances and the conversion rate achieved in the preliminary reactor.

It can also be advantageous to transport into the reactor (42) only a part of the total amount of the acylating agent used and to feed the other part into the reaction column (4) via an additional line (41) below the feed point for the reactor discharge (44). The residence time in the preliminary reactor is advantageously set in such a manner that the reaction is run in a reaction range of high reaction rate.

Generally, the residence time in the upstream reactor (42) is from 5 minutes to 2 hours, preferably from 15 minutes to 1 hour.

The reactor (42) is symbolized in FIG. 2 as a stirred tank. However, depending on the reaction system, reactors having other residence time characteristics, for example tubular reactors or loop reactors are also possible.

Using the inventive improved process it is possible to prepare numerous chromanol ester derivatives, in particular tocopherol acetates and tocotrienol acetates which are of importance as antioxidants and in the human and animal nutrition sectors, in particular α-tocopherol acetate, at virtually quantitative conversion at very high yields and space-time yields and high purity.

The inventive process, compared with the prior art, has the following further advantages:

Using the inventive process, selectivities of greater than 99% are achieved, based on the chromanol derivative, and greater than 90%, based on the carboxylic anhydride. The selectivity based on the carboxylic anhydride is dependent on the purity of the chromanol derivative used, which was 94% in the examples below.

The conversion rate is virtually 100%, based on the chromanol derivative, and 95%, based on the acylating agent, so that only small amounts of acylating agent need to be recirculated.

The purity of the chromanol ester derivatives is greater than 95% after removing carboxylic acid of the formula IIIa and water, or after removing carboxylic anhydride of the formula IIIb and the carboxylic acid R9-COOH. This value is also dependent on the purity of the chromanol derivative of the formula II used, since, in particular in the case of tocopherols and tocotrienols, the product contaminant principally found is high-boiling minor components already present in the tocopherol or tocotrienol used. After removing these components the product purity is greater than 99%, so that only very few byproducts are formed in the inventive process.

A further advantage of the process is the continuous procedure which ensures constant non-charge-dependent product quality. The space-time yield, for comparable acid concentration, is higher by a factor of 3 than in the previously known processes. In addition, the heat of reaction released during the reaction can be utilized for the distillation and thus energy costs can be saved.

A further great advantage of the inventive process is that the high achievable yields are achieved in a continuous process in a reactor with virtually quantitative conversion based on all starting components, more precisely even if no excess, or only a slight excess, of one of the reactants is used.

In addition, advantageously, no solvents need to be used and the carboxylic acid R9-COOH which is formed as a byproduct when carboxylic anhydrides of the formula III are used can be further used as a product of value.

The examples below describe the invention

EXAMPLE 1

Preparation of α-Tocopherol Acetate

A Description of the Apparatus

The apparatus used was a fractionating column (4) having 20 bubble-cap trays (approximately 14 theoretical stages) below the upper feed point (2) and 0.6 meters of a structured mesh packing (Rhombopak 9M) above the upper feed point (2). The column had an internal diameter of 30 mm. The trays were numbered from bottom to top, that is to say the lowest tray was tray 1 and the uppermost tray was tray 20.

The column was fitted with regularly spaced thermocouples, so that in addition to the bottom and the top of the column the temperature could be measured at each 3rd to 4$^{th}$ theoretical stage. In addition to the temperature profile, using appropriate sampling points the concentration profile in the column could be determined.

The evaporator (13) which could be heated using a thermostat to 250° C. had a volume of approximately 350 ml, with the fill level during operation, depending on the residence time, being from 50 to 155 ml. A condenser which was operated by a cryostat was mounted on the column. In addition, the column was equipped with a vacuum system (9) and a cold trap. The bottom discharge (35) of the column was passed to a downstream thin-film evaporator (19), via the bottom of which the crude product (34) freed from low-boilers was ejected. The distillate of the thin-film evaporator was condensed in a condenser (21), collected in a vessel (23) and pumped back to the column. On phase breakdown the vessel (23) was used as separating vessel and the lower phase which contains the carboxylic anhydride was recirculated to the column. The apparatus was run in 24-hour operation (steady state) and all influent and effluent streams were recorded and displayed using balances.

B Experimental Procedure

Preparation of α-Tocopherol Acetate Without Recycling 74.6 g/h (0.16 mol/h) of α-tocopherol (93.6% pure) and 2.05 g/h of 1% strength sulfuric acid in acetic acid (0.13 mol % sulfuric acid (100%) based on α-tocopherol) were pumped to tray 20 of the column and 21.2 g/h (0.34 mol/h) of acetic anhydride were pumped to tray 3 of the column. A system pressure of 400 mbar and a reflux ratio of 2 kg/kg were established.

The bottom temperature was 156° C. and the residence time in the reactor system was 3 hours, which was made up of 1 hour on the internals of the fractionating column (16) and 2 hours in the evaporator (36). The bottoms stream produced from the column was 84.8 g/h of crude product containing 94.0% by weight of α-tocopherol acetate and 0.1% by weight of α-tocopherol. 9.6 g/h of distillate consisting of 100% by weight of acetic acid were taken off from the top of the column.

α-Tocopherol acetate was produced with a selectivity of 99.9% based on α-tocopherol and 96.7% based on acetic anhydride. The conversion rate was 99.9% based on α-tocopherol and 84% based on acetic anhydride. The space-time yield was about 262 g/(l*h).

EXAMPLE 2

Preparation of α-Tocopherol Acetate Without Recirculation/Catalyst to Acetic Anhydride (VEA30)

In the apparatus described in example 1,100.0 g/h (0.22 mol/h) of α-tocopherol (93.6% pure) and 1.9 g/h of 1% strength sulfuric acid in acetic anhydride (0.09 mol % of sulfuric acid (100%) based on α-tocopherol) were pumped to tray 20 of the column and 26.7 g/h (0.26 mol/h) of acetic anhydride were pumped to tray 3 of the column. A system pressure of 400 mbar and a reflux ratio of 2 kg/kg were set. The bottom temperature was 155° C. and the residence time in the reactor system was 2.2 hours, which was made up of 0.7 hours on the fractionating column internals (16) and 1.5 hours in the evaporator (36). The bottoms stream of the column produced was 113.8 g/h of crude product containing 93.7% by weight of α-tocopherol acetate and 0.07% by weight of α-tocopherol. At the top of the column, 11.6 g/h of distillate consisting of 100% by weight of acetic acid were taken off. α-Tocopherol acetate was produced with a selectivity of 99.9% based on α-tocopherol and 97.9% based on acetic anhydride. The conversion rate was 99.9% based on α-tocopherol and 82% based on acetic anhydride. The space-time yield was about 350 g/(l*h).

EXAMPLE 3

Experimental Procedure—Preparation of α-Tocopherol Acetate Using Recirculation (VEA53)

150.0 g/h (0.33 mol/h) of α-tocopherol (94.9% pure) and 2.1 g/h of 1% strength sulfuric acid in acetic anhydride (0.067 mol % sulfuric acid (100%) based on α-tocopherol) were pumped to tray 20 of the column and 35.0 g/h (0.34 mol/h) of acetic anhydride were pumped to tray 3 of the column. A system pressure of 400 mbar and a reflux ratio of 2 kg/kg were set. The bottom temperature was 164° C. and the residence time in the reactor system was 1.2 hours, which was made up of 0.7 hours on the fractionating column internals (16) and 0.5 hours in the evaporator (36). The bottoms stream of the column was passed to the thin-film evaporator, the distillate was condensed out and recirculated into the column to tray 3 (recirculated stream 2.2 g/h). The bottom stream of the thin-film evaporator produced was 164.0 g/h of crude product containing 94.15% by weight of α-tocopherol acetate and 0.34% by weight of α-tocopherol. At the top of the column, 16.4 g/h of distillate consisting of 100% by weight of acetic acid were taken off.

α-Tocopherol acetate was produced with a selectivity of 99.4% based on α-tocopherol and 91.0% based on acetic anhydride. The conversion rate was 99.6% based on α-tocopherol and 100% based on acetic anhydride. The space-time yield was about 700 g/(l*h).

COMPARATIVE EXAMPLE 1

Batchwise Reaction Procedure

The batchwise comparative experiment was carried out in a heated round bottomed flask equipped with stirrer, thermometer and mounted reflux condenser. 300.75 g of α-tocopherol (93.6% pure) (0.655 mol calculated 100%) were charged into the flask and heated to 100° C. 86.4 g (0.847 mol) of acetic anhydride were then admixed with 0.03 g (0.00031 mol) of sulfuric acid (96% strength) and added to the flask with stirring. In the course of this the reaction mixture heated up due to the heat of reaction released and was then controlled to 140° C. After 2 hours the reaction mixture was cooled to room temperature. The reaction discharge was analyzed by GC. 299.7 g of α-tocopherol acetate, 0.05 g of α-tocopherol, 44.3 g of acetic acid and 10.2 g of acetic anhydride were found in the reaction discharge. α-Tocopherol acetate was produced with a selectivity of 96.9% based on α-tocopherol and 85.0% based on acetic anhydride. The conversion rate was 99.9% based on α-tocopherol and 88% by weight based on acetic anhydride. The total batch time was about 3 hours.

We claim:

1. A process for continuously preparing chromanol ester of the formula I,

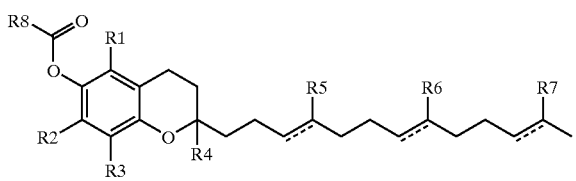

where

R1, R2, R3, R4, R5, R6, R7 and R8 independently of one another are hydrogen or an unsubstituted or substituted, branched or unbranched $C_1$–$C_{10}$-alkyl radical and the dashed bonds are a possible additional C—C bond, by reacting continuously fed chromanol of the formula II

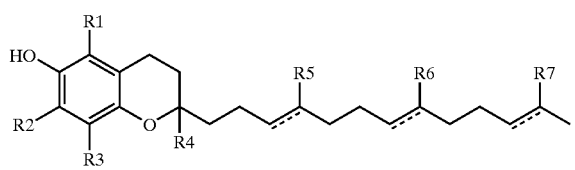

with continuously fed an acylating agent selected from the group consisting of carboxylic acids of the formula IIIa

                  IIIa and carboxylic anhydrides of the formula IIIb,

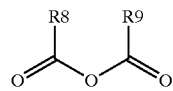                  IIIb where

R9 is hydrogen or an unsubstituted or substituted, branched or unbranched $C_1$–$C_{10}$-alkyl radical, and R8 is as defined above, in a reactor and continuously removing the reaction products from the reactor.

2. A process as claimed in claim 1, wherein at least one reaction product is removed from the reaction mixture during the reaction.

3. A process as claimed in claim 1, wherein the reactor is a reaction column.

4. A process as claimed in claim 3, wherein the reaction parameters are set in such a manner that A the chromanol of the formula II react with the acylating agent on the internals and possibly in the bottom phase of the reaction column, B the $H_2O$ formed in the reaction with the carboxylic acids of the formula IIIa or the carboxylic acid R9-COOH formed in the reaction with the carboxylic anhydrides of the formula IIIb is continuously removed with the overhead stream of the reaction column and C the chromanol ester of the formula I formed in the reaction are continuously removed with the bottom stream of the reaction column.

5. A process as claimed in claim 3, wherein a further reactor is connected upstream of the reaction column.

6. A process as claimed in claim 1, wherein the reaction is carried out in the presence of a catalyst.

7. A process as claimed in claim 3, wherein the reaction column has internals in form of column trays below the highest feed point for the reactants, and internals in form of structured packings above the highest feed point for the reactants.

8. A process as claimed in claim 3, wherein the reactants of formula II and of formula IIIa or formula IIIb are separately fed into the reaction column at different points, the reactant having a higher boiling point, optionally together with a catalyst, being fed into the reaction column at a point above the point at which the lower-boiling reactant is fed to the column.

9. A process as claimed in claim 3, wherein heat is fed into the reaction column by means of an evaporator and additionally by means of heat exchangers mounted externally to the reaction column, or by means of heat exchangers situated directly on internals of the reaction column.

10. A process as claimed in claim 3, wherein a stripping gas is introduced into the reaction column.

11. A process as claimed in claim 3, wherein excess acylating agent is separated from the effluent bottom stream in a downstream evaporator, and the separated acylating agent is, in whole or in part, recirculated to the column.

12. A process as claimed in claim 1, wherein the reactor comprises a preliminary reactor and a reaction column, said preliminary reactor being connected upstream to the reaction column.

13. A process as claimed in claim 12, wherein heat is fed into the reaction column by means of an evaporator and additionally by means of heat exchangers mounted externally to the reaction column, or by means of heat exchangers situated directly on internals of the reaction column, and heat is additionally supplied to said preliminary reactor.

* * * * *